US006746664B2

(12) United States Patent
Allred

(10) Patent No.: US 6,746,664 B2
(45) Date of Patent: *Jun. 8, 2004

(54) MULTI-PART DENTAL BLEACHING SYSTEMS AND METHODS FOR BLEACHING TEETH USING SUCH SYSTEMS

(75) Inventor: Peter M. Allred, Riverton, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/212,381

(22) Filed: Aug. 5, 2002

(65) Prior Publication Data
US 2003/0082115 A1 May 1, 2003

Related U.S. Application Data

(63) Continuation-in-part of application No. 09/923,049, filed on Aug. 6, 2001, now Pat. No. 6,503,485.

(51) Int. Cl.[7] .............................. A61K 7/16; A61K 7/20
(52) U.S. Cl. .............................. 424/53; 424/49; 433/90; 433/141; 433/164; 433/216
(58) Field of Search ....................... 424/49, 53; 433/90, 433/141, 164, 216

(56) References Cited

U.S. PATENT DOCUMENTS

| | | | |
|---|---|---|---|
| 4,788,052 A | 11/1988 | Ng et al. .................... | 424/53 |
| 4,839,156 A | 6/1989 | Ng et al. .................... | 424/53 |
| 4,839,157 A | 6/1989 | Mei-King Ng et al. ........ | 424/53 |
| 4,971,782 A | 11/1990 | Rudy et al. ................. | 424/53 |
| 4,976,955 A | 12/1990 | Libin ........................ | 424/53 |
| 5,032,178 A | 7/1991 | Cornell ..................... | 106/35 |
| 5,122,365 A | 6/1992 | Murayama ................... | 424/49 |
| 5,171,564 A | 12/1992 | Nathoo et al. ............... | 424/53 |
| 5,240,415 A | 8/1993 | Haynie ..................... | 433/216 |
| 5,376,006 A | 12/1994 | Fischer .................... | 433/215 |
| 5,401,495 A | 3/1995 | Murayama ................... | 424/49 |
| 5,597,554 A | 1/1997 | Wagner ..................... | 424/53 |
| 5,614,174 A | 3/1997 | Hsu et al. .................. | 424/49 |
| 5,631,000 A | 5/1997 | Pellico et al. .............. | 424/53 |
| 5,645,428 A | 7/1997 | Yarborough ................. | 433/215 |
| 5,648,064 A | 7/1997 | Gaffar et al. .............. | 424/53 |
| 5,713,738 A | 2/1998 | Yarborough ................. | 433/215 |
| 5,718,886 A | 2/1998 | Pellico .................... | 424/53 |
| 5,759,031 A | 6/1998 | Goldsmith et al. ........... | 433/29 |
| 5,759,038 A | 6/1998 | Fischer .................... | 433/215 |
| 5,766,011 A | 6/1998 | Sibner ..................... | 433/215 |
| 5,766,574 A | 6/1998 | Christina-Beck et al. ..... | 424/53 |
| 5,785,527 A | 7/1998 | Jensen et al. .............. | 433/215 |
| 5,819,988 A | 10/1998 | Sawhney et al. ............. | 222/137 |
| 5,820,854 A | 10/1998 | Glandorf ................... | 424/52 |
| 5,858,332 A | 1/1999 | Jensen et al. .............. | 424/53 |
| 5,902,568 A | 5/1999 | Ryles et al. ............... | 424/53 |
| 5,922,307 A | 7/1999 | Montgomery ................. | 424/53 |
| 5,928,628 A | 7/1999 | Pellico .................... | 424/49 |
| 5,976,508 A | 11/1999 | Nabi et al. ................ | 424/53 |
| 6,036,493 A | 3/2000 | Sharma ..................... | 433/216 |
| 6,065,645 A | 5/2000 | Sawhney et al. ............. | 222/137 |
| 6,106,812 A | 8/2000 | Prencipe et al. ............ | 424/53 |
| 6,110,446 A | 8/2000 | Prencipe et al. ............ | 424/53 |
| 6,116,900 A | 9/2000 | Ostler ..................... | 433/89 |
| 6,162,055 A | 12/2000 | Montgomery et al. .......... | 433/216 |
| 6,174,516 B1 | 1/2001 | Curtis et al. .............. | 424/53 |
| 6,280,708 B1 | 8/2001 | Ryles et al. ............... | 424/53 |
| 6,306,370 B1 | 10/2001 | Jensen et al. .............. | 424/49 |
| 6,309,625 B1 | 10/2001 | Jensen et al. .............. | 424/49 |
| 6,312,666 B1 | 11/2001 | Oxman et al. ............... | 424/49 |
| 6,312,670 B1 | 11/2001 | Montgomery ................. | 424/53 |
| 6,312,671 B1 | 11/2001 | Jensen et al. .............. | 424/53 |
| 6,322,773 B1 | 11/2001 | Montgomery ................. | 424/53 |
| 6,322,774 B1 | 11/2001 | Jensen et al. .............. | 424/53 |
| 6,343,933 B1 | 2/2002 | Montgomery et al. .......... | 433/216 |
| 6,354,837 B1 | 3/2002 | Jensen ..................... | 433/215 |
| 6,365,134 B1 | 4/2002 | Orlowski et al. ............ | 424/53 |
| 6,368,576 B1 | 4/2002 | Jensen et al. .............. | 424/49 |
| 6,394,314 B1 | 5/2002 | Sawhney et al. ............. | 222/137 |

FOREIGN PATENT DOCUMENTS

WO    WO 01/17481    3/2001

OTHER PUBLICATIONS

"Opalescence® Xtra Boost", Two– Part System contains one Syringe of 38% Hydrogen Peroxide the Other a Unique Proprietary Chemical Activator that Increases the Ph to 7.0, www.ultradent.com, Apr. 30, 2002, 2 pages.

Discus Dental Website, Nite White Excel 2 NSF 100% standard kit, dual chambered syringe, First Chamber Hydrogen & Carbamide Peroxide, Daywhite, 227.5% Hydrogen Peroxide, Jul. 11, 2002, 7 pages.

Primary Examiner—Frederick F. Krass
(74) Attorney, Agent, or Firm—Workman Nydegger

(57) ABSTRACT

Dental bleaching systems that include a bleaching component and a neutralizing component which, when mixed together, yield a mixed composition having a desired bleaching activity and gel properties. The bleaching composition includes a suitable bleaching agent, such as aqueous hydrogen peroxide, in a concentration of about 3% to about 95% by weight of the bleaching composition component. The neutralizing component includes a strong particulate base mixed with a polymeric thickening agent. The neutralizing component is substantially water-free to prevent destruction of the gelling capability of the thickening agent by the base prior to formation of the mixed composition. The particulate base may include oxides, hydroxides or carbonates of alkali metals or alkaline earth metals. Maintaining the bleaching agent and neutralizing agent in separate components provides increased stability of both the bleaching agent and gelling (thickening) agent during storage and transport.

31 Claims, No Drawings

MULTI-PART DENTAL BLEACHING SYSTEMS AND METHODS FOR BLEACHING TEETH USING SUCH SYSTEMS

RELATED APPLICATION

This application is a continuation-in-part of U.S. application Ser. No. 09/923,049, filed Aug. 6, 2001, now U.S. Pat. No. 6,503,485. For purposes of disclosure, the foregoing application is incorporated herein by reference.

BACKGROUND OF THE INVENTION

1. The Field of the Invention

This invention is in the field of compositions and methods for bleaching teeth. More particularly, the invention is in the field of compositions and methods for accelerated bleaching activity using a two-part bleaching system. A first part includes a stable concentrated dental bleaching agent at low pH and a second part includes a dry particulate base mixed with a gelling agent.

2. The Relevant Technology

In the last decade there has been a proliferation of compositions and methods for bleaching teeth. Compositions for both in-office or at-home use typically include a peroxide bleaching agent, such as carbamide peroxide or aqueous hydrogen peroxide. Carbamide peroxide is a complex of urea and molecular hydrogen peroxide. On the other hand, hydrogen peroxide by itself only exists in aqueous form and is generally unstable except at relatively low pH (e.g., 2).

When formulating an appropriate bleaching composition there is inherently a trade-off between stability and reactivity. It is desirable for a bleaching composition to remain stable between the time when it is manufactured and when it is used to bleach a person's teeth. However, once placed on a person's teeth it is desirable for the composition to quickly break down and release active oxygen radicals capable of bleaching teeth. One way to obtain long-term stability is to keep the concentration of active bleaching agent relatively low. This, however, has the negative drawback of providing only minimal to modest bleaching activity.

Dental bleaching compositions that include higher concentrations of dental bleaching agent must generally be kept refrigerated to ensure long-term stability and/or kept at relatively low pH (e.g., 2 or less) where refrigeration cannot be guaranteed. In the case where it is desired to mass-produce a highly concentrated dental bleaching composition and then distribute it to many different locations, it is generally impossible to prevent at least a portion of such composition from becoming overheated at some point during shipping and handling. Unless such compositions are maintained at a low pH, their potency can be compromised if they are exposed to excessive heat during shipping. Accordingly, it has heretofore been difficult to manufacture and then distribute bleaching compositions at higher pH (e.g., neutral pH) that include high concentrations of bleaching agent while avoiding at least partial breakdown of the bleaching agent.

Since highly acidic compositions can etch or otherwise damage teeth if maintained in contact with the teeth for more than a few minutes, it is typically desirable to neutralize an acidic bleaching composition prior to application to a patient's teeth. In the case where the composition to be applied to the patient's teeth is intended to have a generally aqueous, non-viscous consistency, neutralization of an acidic aqueous hydrogen peroxide solution by means of a base is straightforward. One simple neutralization method is to add aqueous sodium hydroxide to the aqueous hydrogen peroxide until the pH is raised to the desired level. Depending on the concentration of the hydrogen peroxide and the resulting pH, raising the pH can also have the desired benefit of at least partially destabilizing the hydrogen peroxide so as to accelerate the release of oxygen radicals responsible for bleaching teeth.

Besides sodium hydroxide, there are a variety of bases or buffers that have been used to neutralize the acidity of stable hydrogen peroxide compositions. U.S. Pat. Nos. 5,713,738 and 5,645,428 to Yarborough, for example, discloses the use of sodium carbonate, sodium bicarbonate, calcium carbonate, ammonium hydroxide, potassium hydroxide, or calcium hydroxide to raise the pH of aqueous bleaching compositions so as to accelerate bleaching activity. For purposes of disclosing bases for use in neutralizing acidic hydrogen peroxide compositions, the foregoing patents are incorporated herein by reference.

One of the challenges in manufacturing two-part bleaching systems having an acidic bleaching component and a strong basic component, which are mixed together by the dental practitioner, is the difficulty in obtaining stable gels. Gels are often desirable over runny compositions because they adhere much better to the patient's teeth compared to non-viscous liquids and stay in place rather than running off the teeth and onto surrounding soft oral tissues. Gels having a certain level of stickiness and viscosity are also desirable when using custom-fitting dental trays known in the art and exemplified by those disclosed in U.S. Pat. No. 5,376,006. For purposes of disclosing custom dental trays for bleaching teeth, the foregoing patent is incorporated herein by reference.

The ability to obtain a stable gel is particularly difficult where it is desired to use a polymeric tackifying agent such as carboxypolymethylene. Carboxypolymethylene is unable to maintain its desired stickiness and gelling capabilities over time when mixed with either concentrated acidic aqueous hydrogen peroxide solutions or strongly basic solutions used to neutralize the acidic hydrogen peroxide solution. Where it is desired to mass produce highly concentrated yet stable hydrogen peroxide bleaching compositions, it has heretofore been necessary to entirely replace carboxypolymethylene and like polymers with non-polymeric thickeners such as fumed silica in order to obtain stable gels.

In view of the foregoing, it would be an advancement in the art to provide improved two-part dental bleaching systems and methods of manufacturing such systems in order to yield a mixed composition that includes a polymeric thickening agent.

Such compositions and methods for providing multi-part dental bleaching systems yield a final mixed composition having a relatively high concentration of active hydrogen peroxide and a polymeric thickening agent are disclosed and claimed herein.

SUMMARY OF THE INVENTION

The present invention relates to dental bleaching systems and methods for manufacturing and using such bleaching systems to bleach teeth. More particularly, the invention encompasses multi-part dental bleaching systems that comprise a first part comprising a concentrated and stable acidic dental bleaching composition and a second part comprising a particulate base mixed together with a polymeric thickening agent as a neutralizing composition. Upon mixing the components together, the particulate base mixes with and raises the pH of the initially acidic bleaching composition, while the polymeric thickening agent yields a final gelled composition having desired stickiness, viscosity and other gel properties.

The multi-part system both preserves bleaching potency and ultimate stickiness or other gel properties of the final mixed composition during transport and subsequent storage. In other words, even after transport and storage, upon mixing the parts together a bleaching gel composition having a desired bleaching potency and gel properties can be formed. This allows the multi-part composition to be manufactured and then shipped and stored as desired prior to mixing the parts together without any significant loss in bleaching potency and destruction of ultimate gel properties. The invention also encompasses methods of manufacturing the inventive multi-part dental bleaching systems, as well as methods for bleaching a person's teeth using such systems.

A first part or composition of the inventive dental bleaching system includes a dental bleaching agent. There are a variety of dental bleaching agents capable of releasing oxygen radicals. The most commonly used dental bleaching agents are based on hydrogen peroxide, including aqueous hydrogen peroxide or complexes of hydrogen peroxide, such as urea peroxide or a perborate (e.g., sodium perborate monohydrate). Sodium perborate monohydrate is a complex of sodium borate and molecular hydrogen peroxide. In one embodiment, the dental bleaching agent will advantageously comprise a concentrated aqueous solution of hydrogen peroxide (e.g., about 20–90% hydrogen peroxide, preferably about 30–60% hydrogen peroxide).

The pH of the first part or composition (i.e., the part that includes the dental bleaching agent) will typically be on the acidic side of the pH scale, generally less than about 5. In order to maintain the stability of the first part or component, particularly in the case where constant refrigeration cannot be ensured, it may be desirable to adjust the pH to below about 4, preferably to below about 3, and more preferably to a pH between about 1–2. The naturally low pH of aqueous hydrogen peroxide solutions can further be lowered by adding one or more acids in order to further increase stability (e.g., citric acid, which can also act as an ion scavenger).

The first part or composition may include optional additives in addition to the dental bleaching agent such as ion scavengers (e.g. EDTA or citric acid) or other stabilizing agents, thickening agents that are stable in the presence of hydrogen peroxide and/or low pH (e.g., fumed silica or gums), liquid polyols (e.g. PEG), and light-energy absorbing agents (e.g. carotene). Highly concentrated hydrogen peroxide bleaching compositions containing a variety of optional additives and adjuvents are set forth in U.S. Pat. No. 5,858,332 to Jensen et al. For purposes of disclosing highly concentrated dental bleaching compositions, as well as adjuvents and additives that may be included within such compositions, the foregoing patent is incorporated herein by reference.

A second part or composition of the inventive bleaching systems according to the invention includes a strong base in particulate form mixed with a polymeric thickening agent in a manner so as to preserve the ability of the thickening agent to impart desired thickening and tackifying properties when mixed with the bleaching composition to form the mixed composition. The neutralizing composition may be in many desired forms, e.g., a gel, a mixture of dry powders or particulates, or a paste. Examples of suitable bases include oxides, hydroxides, and carbonates of alkali and alkaline earth metals (e.g., finely ground potassium hydroxide or calcium carbonate). Examples of suitable polymeric thickening agents include carboxypolymethylene (which broadly includes carboxypolymethylene at any pH and at any degree of neutralization), PEMULEN (a proprietary composition available from B. F. Goodrich), and compositional or chemical equivalents thereof. The second part may optionally include additional components such as ion scavengers, other thickening agents, liquid polyols, and light-energy absorbing agents.

In order to prevent base-catalyzed destruction of the polymeric thickening agent, it is typically advantageous for the second part or composition to be substantially water free, preferably essentially anhydrous, since water is believed to hydrolyze or otherwise affect the stability of the polymeric thickening agent when mixed with a strong base. Because the second part is essentially water free, it does not technically have a pH. However, due to the inclusion of a strong base, the pH of the second part is hypothetically about 11–14 if mixed with sufficient water to produce an actual pH reading.

Upon mixing the first and second parts together, typically by the dental practitioner who will administer the bleaching composition to a patient's teeth, the neutralizing component raises the pH of the bleaching agent so as to yield a mixed composition having a pH between about 4 and 11, more preferably between about 5 and 9, and most preferably between about 6 and 8. After mixing the multiple parts together, the mixed composition may either be used immediately by the dental practitioner for bleaching or else stored for later use, typically under refrigeration. Depending on the concentration of the dental bleaching agent, and/or the pH of the resulting mixed composition, and/or whether the mixed composition includes other components that affect the stability (e.g., stabilizing or destabilizing agents), the dental practitioner can optimize or adjust the stability of the mixed dental bleaching composition to suit the particular needs of the dental practitioner.

The relative stability or instability of the mixed dental bleaching composition depends, at least in part, on the pH, the temperature, and the relative concentration of the bleaching agent in the mixed composition. In general, the higher the pH and warmer the temperature, the less stable will be the bleaching agent at a given concentration. Accordingly, where it is desired to accelerate bleaching activity, the dental practitioner may wish to further raise the pH of the mixed composition in order to trigger the release of oxygen radicals, which are believed to be responsible for bleaching teeth. On the other hand, where it is desired to form a batch of mixed bleaching composition that can be stored in refrigeration for later use, it may be desirable to keep the pH at a level that does not trigger the release of oxygen radicals for a given concentration of bleaching agent.

The polymeric thickening agent within the neutralizing composition imparts a desired stickiness, tackiness, viscosity or other gel or thickening properties to the final mixed composition. Maintaining the neutralizing composition in substantially moisture free (e.g., less than about 1% unbound water) helps prevent the polymeric thickening agent from prematurely breaking down or hydrolyzing prior to formation of the final mixed composition.

The mixed composition will typically be used by dental practitioners during in-office procedures. This is particularly true for mixed compositions having relatively high concentrations of dental bleaching agent (e.g., about 20–90% available hydrogen peroxide), which are typically not suitable for at-home use. Nevertheless, the compositions of the present invention are not limited to any particular use or application and broadly include any two- or multi-part dental bleaching system that includes a bleaching agent in one part and a strong base dispersed within a stable gel in another part. Thus, home use products that incorporate the inventive multi-part bleaching systems disclosed herein are certainly within the scope of the invention.

These and other features of the present invention will become more fully apparent from the following description and appended claims, or may be learned by the practice of the invention as set forth hereinafter.

DETAILED DESCRIPTION OF THE PREFERRED EMBODIMENTS

I. INTRODUCTION

The present invention relates to dental bleaching systems and methods for manufacturing and using such systems to bleach teeth. More particularly, the invention encompasses multi-part dental bleaching systems that comprise a first part (or composition) that includes a concentrated and stable dental bleaching agent and a second part (or composition) that includes a strong base mixed with a polymeric thickening agent in a manner so as to preserve the ability of the thickening agent to impart desired stickiness, viscosity and other gel properties to the final mixed composition.

The multi-part systems are stable over time with respect to ultimate bleaching potency, stickiness, viscosity, and gelation in the final mixed composition. Keeping the first part containing the bleaching agent at a lower pH helps maintain bleaching potency during transport and storage. Similarly, maintaining the second part substantially free of water (i.e., unbound water that is available for hydrolysis) helps to maintain the desired gelling properties of the polymeric thickening agent. Consequently, upon mixing the two parts together, a bleaching gel having a desired bleaching potency and gel properties can be formed. This allows the two-part composition to be manufactured and then shipped and stored as desired prior to mixing the parts together without any significant loss in bleaching potency and the breakdown of the gelation properties of the polymeric thickening agent by the strong base.

The invention also encompasses methods of manufacturing the inventive multi-part dental bleaching systems, as well as methods for bleaching a person's teeth using such systems.

II. MULTI-PART DENTAL BLEACHING SYSTEMS

The dental bleaching systems according to the present invention include at least two different parts or compositions that are manufactured and advantageously stored and transported separately so as to maximize the desired properties of the final mixed composition, as noted above. At a minimum, a first part or component will include a dental bleaching agent, preferably in concentrated form, and at preferably low pH (e.g., <4). A second part or composition will include a base mixed with a polymeric thickening agent. The two parts or compositions may include other additives or adjuvents as desired to yield mixed compositions that have desired properties. It is also within the scope of the invention to include additional parts or compositions that can be mixed with parts one and two which are discussed more fully below.

A. Part One: Bleaching Composition.

A first part (bleaching composition) of the inventive dental bleaching system includes a dental bleaching agent. There are a variety of dental bleaching agents capable of releasing oxygen radicals. The most commonly used dental bleaching agents are based on hydrogen peroxide. Examples include aqueous hydrogen peroxide and complexes of hydrogen peroxide, such as urea peroxide, perborates (e.g. sodium perborate monohydrate), and peroxyacetic acid. Sodium perborate monohydrate is a complex of sodium borate and molecular hydrogen peroxide.

The dental bleaching agent may be included in any amount so as to yield a mixed composition having a desired concentration and potency. In general, the multi-component systems of the present invention are particularly useful in maintaining the bleaching strength of bleaching agents that are contained in higher concentrations. In general, the concentration of available hydrogen peroxide may range from as low as 3% to as high as 95% by weight of the bleaching composition (i.e., part one), preferably in a range from about 20% to about 90% by weight, more preferably in a range from about 30% to about 70% by weight, most preferably in a range from about 40% to about 60% by weight of the bleaching composition. In a presently preferred embodiment, the bleaching agent includes aqueous hydrogen peroxide. Nevertheless, it is certainly within the scope of the invention to augment or substitute some or all of the aqueous hydrogen peroxide with any other known bleaching agent.

The dental bleaching agent may advantageously be mixed with other components as desired to yield a bleaching component having the desired properties. For example, it may be desirable to include one or more polyols such as glycerin, sorbitol, propylene glycol, polypropylene glycol, and polyethylene glycol within part one. Thickeners that are stable in the presence of strong bleaching agents and low pH may also be included, an example of which is fumed silica. Ion scavengers (e.g. EDTA and citric acid) or other stabilizing agents, other thickening agents (e.g., gums), flavorants, and light-energy absorbing agents (e.g. carotene) may be included as desired.

The pH of the bleaching part or composition will typically be on the acidic side of the pH scale, generally less than about 5. In order to maintain the stability of the first part or component, particularly in the case where constant refrigeration cannot be ensured, it may be desirable to adjust the pH to below about 4, preferably to below about 3, and more preferably to a pH between about 1–2. Aqueous hydrogen peroxide naturally results in a low pH solution, although commercial grades of hydrogen peroxide may include a strong acid to further lower the pH to a desired level. Citric acid can stabilize the peroxide by both lowering the pH and acting as an ion scavenger.

The bleaching part or component is preferably substantially free of abrasives, since abrasives (otherwise known as polishing agents) common to toothpastes may trigger or catalyze the destabilization of the dental bleaching agent. Nevertheless, it is certainly within the scope of the invention to include an abrasive if desired.

B. Part Two: Neutralizing Composition

A second part (neutralizing composition) of the inventive bleaching systems according to the invention includes a strong base mixed with a polymeric thickening agent in a manner so as to preserve the thickening, tackifying, and viscosity enhancing and/or other gelling properties of the thickening agent. The base is advantageously in a nonsolubilized and particulate form to prevent or reduce any negative reactions between the base and thickening agent. The neutralizing composition is essentially moisture-free in order to prevent hydrolysis of the polymeric thickening agent by the base (e.g., preferably less than about 1% unbound water, more preferably less than about 0.5% unbound water, most preferably less than about 0.19% unbound water). Thus, the neutralizing composition is preferably essentially anhydrous.

The base may be obtained in powder form, or it may be obtained as pellets or flakes and subsequently ground using any appropriate grinding means and methods known in the art (e.g., wet grinding using an appropriate liquid and a grinding mill). Examples of suitable bases include oxides, hydroxides, and carbonates of alkali and alkaline earth metals, as well as ammonium hydroxide, which are crystalline solids and which can be ground into fine powders and dispersed in particulate form within a gel that is substantially free of water. The concentration or amount of added base may be selected so as to yield a final mix composition having a desired pH. Because the pH of the final composition depends on a variety of factors, such as the pH of the bleaching part or component, the desired pH of the mixed composition, the relative quantities of parts one and two, and the concentration, if any, of any additional components added to the final mixture, as well as the relative strength of the base, there is no preferred concentration range for the base within the neutralizing composition.

A wide variety of thickening agents may be used within the scope of the invention, including both polymeric thickening agents and finely divided particulates. The second part or composition will, at a minimum, include at least one polymeric thickening agent. Examples of suitable polymeric thickening agents include carboxypolymethylene, PEMULEN, PLURONIC, cellulosic ethers, polysaccharide gums, proteins, starches, and the like. The second part may also include additional components such as ion scavengers (e.g., EDTA), particulate thickening agents (e.g., fumed silica), liquid polyols, and light-energy absorbing agents (e.g., carotene).

Carboxypolymethylene is a well-known thickening agent utilized in dental bleaching compositions and a wide variety of other compositions. It is a slightly acidic vinyl polymer with active carboxyl groups. Suitable carboxypolymethylene compositions may be obtained from B. F. Goodrich Co. under the trade name CARBOPOL. For purposes of this disclosure and the appended claims, the term "carboxypolymethylene" shall broadly include carboxypolymethylene at any pH and any degree of neutralization with a base.

One currently preferred carboxypolymethylene resin is known by the trade name CARBOPOL 934P. CARBOPOL 934P is a high purity pharmaceutical grade of CARBOPOL 934, having an approximate molecular weight of about 3 million. Another preferred carboxypolymethylene is CARBOPOL 974P NF, which has more recently surpassed CARBOPOL 934P as the carboxypolymethylene of choice in many compositions.

PEMULEN is a trade name of B. F. Goodrich and is used to identify high molecular weight, cross-linked copolymers of acrylic acid and a hydrophobic comonomer. The exact composition of PEMULEN is unknown since it is a proprietary formulation of B. F. Goodrich.

The name PLURONIC describes a range of polymers available from BASF, which are also known as poloxamers. The term "poloxamer" is the CFTA name for polyoxyethylene polyoxypropylene block copolymers. An example includes POLOXOMER407, also known as PLURONIC F127.

Then neutralizing composition may have any desired form, such as a mixture of dry ingredients, a gel or a paste, where it is desired for the neutralizing composition to be a stable gel, the second part or component will also typically include an appropriate solvent for the polymeric gelling agent, such as a liquid polyol. Examples of suitable polyols include, but are not limited to, glycerin, propylene glycol, polypropylene glycol, polyethylene glycol, sorbitol, and the like.

In order to preserve the gelling ability of the polymeric thickening agent, it is typically advantageous for the second part or composition to be substantially water free, preferably essentially anhydrous, since water is believed to hydrolyze or otherwise affect the stability of the polymeric thickening agent when mixed with a strong base. Because the second part is essentially water free, it does not technically have a pH. However, due to the inclusion of a strong base, the pH of the second part is hypothetically about 11-14 if mixed with sufficient water to produce an actual pH reading. It is also preferable for the second part to be substantially free of abrasives, although it would certainly be within the scope of the invention to include an abrasion.

C. Mixed Composition

In general, the relative concentrations of the bleaching composition and the neutralizing composition will range from about 1:2 to about 10:1, preferably about 1:1 to about 5:1. Nevertheless, it is within the scope of the invention to utilize the bleaching and neutralizing compositions in any desired ratio that yields a desired mixed composition. In general, it will be advantageous for the bleaching composition to predominate in order to obtain a final mixed composition having a relatively high concentration of bleaching agent. In general, a smaller quantity of a strong base can be used to neutralize a greater quantity of the more weakly acidic bleaching composition, such that it may be feasible for the ratio of the bleaching composition to neutralizing composition to be as high as about 10:1 or more.

Upon mixing the bleaching and neutralizing compositions together, typically by the dental practitioner who will administer the bleaching composition to a patient's teeth, the neutralizing composition raises the pH of the bleaching composition so as to yield a mixed composition having a pH between about 4 and 11, more preferably between about 5 and 9, and most preferably between about 6 and 8. After mixing the multiple parts together, the mixed composition may either be used immediately by the dental practitioner for bleaching or else stored for later use, typically under refrigeration. Depending on the concentration of the dental bleaching agent, and/or the pH of the resulting mixed composition, and/or whether the mixed composition includes other components that affect the stability (e.g., stabilizing or destabilizing agents), the dental practitioner can optimize or adjust the stability of the mixed dental bleaching composition to suit the particular needs of the dental practitioner.

The relative stability or instability of the mixed dental bleaching composition depends, at least in part, on the pH, the temperature, and the relative concentration of the bleaching agent in the mixed composition. In general, the higher the pH and warmer the temperature, the less stable will be the bleaching agent at a given concentration. Accordingly, where it is desired to accelerate bleaching activity, the dental practitioner may wish to further raise the pH of the mixed composition in order to trigger the release of oxygen radicals, which are believed to be responsible for bleaching teeth. On the other hand, where it is desired to form a batch of mixed bleaching composition that can be stored for later use, it may be desirable to keep the pH at a level that does not trigger the release of oxygen radicals for a given concentration of bleaching agent and at the expected storage temperature. The mixed compositions of the invention will preferably be substantially or entirely free of abrasives, although the use of an abrasive is not foreclosed.

The polymeric thickening agent imparts a desired stickiness, tackiness, viscosity or other gel or thickening properties to the final mixed composition. Maintaining the neutralizing composition substantially moisture free (e.g., less than about 1% unbound water) helps prevent the polymeric thickening agent from prematurely breaking down or hydrolyzing prior to formation of the final mixed composition. The term "unbound water" refers to water that is actually free to enter into and be consumed in a hydrolysis reaction involving the polymeric thickening agent.

III. METHODS OF USE

The mixed compositions will typically be used by dental practitioners during in-office procedures. This is particularly true for mixed compositions having relatively high concentrations of dental bleaching agent (e.g., about 20–90% available hydrogen peroxide), which are typically not suitable for at-home use. Nevertheless, the compositions of the present invention are not limited to any particular use or application and broadly include any use that involves two- or multi-part dental bleaching systems that include a bleaching agent in one part and a strong base dispersed within a stable gel in another part. Thus, home-use products that incorporate the inventive multi-part bleaching systems disclosed herein are certainly within the scope of the invention.

Whereas raising the pH of the mixed composition generally accelerates the bleaching activity of the dental bleaching agent, it may be further desirable for the dental practitioner to further accelerate the bleaching activity by applying light or heat energy (e.g., by means of a dental curing light, a heat lamp, a dental light guide, or a laser). The inclusion of carotene or other light energy absorbing agents within the mixed composition facilitates the acceleration of bleaching activity through the application of radiant energy.

In the case where the mixed composition is used in an at-home bleaching regimen, it will be preferable to apply the composition using a soft, flexible, custom-fitting dental tray known in the art. Nevertheless, it should be understood that any dental tray known in the art, even thick athletic mouth guards and the like, may be used to apply the dental bleaching compositions according to the present invention.

IV. EXAMPLES

In order to better illustrate the types of compositions contemplated within the multi-part dental bleaching systems according to the invention, the following examples are given.

Example 1

A two-part dental bleaching system was made that included the following components within each of Parts 1 and 2.

| Part 1 | Part 2 | |
|---|---|---|
| Aqueous hydrogen peroxide (50%) | Propylene Glycol | 82 g |
| | PEMULEN | 3.6 g |
| | Potassium hydroxide | 1.35 g |
| | Carotene | 1.8 g |

Part 1 had a pH below about 2 and was stable against degradation over time. The inclusion of PEMULEN within Part 2 resulted in a stable viscous gel that did not degrade over time in the presence of potassium hydroxide. The gel stability of PEMULEN in the presence of potassium hydroxide was believed to be due to the fact that Part 2 was substantially free of water.

Upon mixing Parts 1 and 2 together in a ratio of 70.5% by weight of Part 1 to 29.5% by weight of Part 2, the potassium hydroxide acted as a water soluble pH buffer that adjusted the pH of the final mixed composition to within an acceptable range. The gelling properties of PEMULEN remained stable for a few weeks within the mixed composition.

Example 2

A two-part dental bleaching system was made that included the following components within each of Parts 1 and 2.

| Part 1 | Part 2 | |
|---|---|---|
| Aqueous hydrogen peroxide (50%) | Propylene Glycol | 78.3 g |
| | PEMULEN | 5.4 g |
| | Potassium hydroxide | 1.8 g |
| | Carotene | 3.0 g |

Part 1 had a pH below about 2 and was stable against degradation over time. The inclusion of PEMULEN within Part 2 resulted in a stable viscous gel that did not degrade over time in the presence of potassium hydroxide. The viscosity of Part 2 was substantially greater than the viscosity of Part 2 of Example 1 due to inclusion of an increased quantity of PEMULEN.

Upon mixing Parts 1 and 2 together in a ratio of 70.5% by weight of Part 1 to 29.5% by weight of Part 2, the potassium hydroxide acted as a water soluble pH buffer that adjusted the pH of the final mixed composition to approximately 4. The gelling properties of PEMULEN remained stable for a few weeks within the mixed composition, although some separation of Part 2 was observed over time.

Example 3

A two-part dental bleaching system was made that included the following components within each of Parts 1 and 2.

| Part 1 | Part 2 | |
|---|---|---|
| Aqueous hydrogen peroxide (50%) | Glycerin | 81 g |
| | PEMULEN | 2.4 g |
| | Potassium hydroxide | 2.1 g |
| | Carotene | 3.0 g |

Part 1 had a pH below about 2 and was stable against degradation over time. The inclusion of PEMULEN within Part 2 resulted in a stable viscous gel that did not degrade over time in the presence of potassium hydroxide. The viscosity of Part 2 was less than that of Part 2 of either Example 1 or Example 2. The potassium hydroxide was initially obtained as flakes and subsequently ground together with the glycerin within a grinding mill to yield a finely ground particulate slurry.

Upon mixing Parts 1 and 2 together in a ratio of 70.5% by weight of Part 1 to 29.5% by weight of Part 2, the potassium hydroxide acted as a water soluble pH buffer that adjusted the pH of the final mixed composition to within an acceptable range. The gelling properties of PEMULEN remained stable for a few weeks within the mixed composition.

Example 4

A two-part dental bleaching system was made that included the following components within each of Parts 1 and 2.

| Part 1 | Part 2 | |
|---|---|---|
| Aqueous hydrogen peroxide (50%) | Glycerin | 78 g |
| | CARBOPOL 974 | 5.4 g |
| | Potassium hydroxide | 2.1 g |
| | Carotene | 3.0 g |

Part 1 had a pH below about 2 and was stable against degradation over time. The inclusion of CARBOPOL 974 within Part 2 resulted in a stable viscous gel that did not degrade over time in the presence of potassium hydroxide.

Upon mixing Parts 1 and 2 together in a ratio of 70.5% by weight of Part 1 to 29.5% by weight of Part 2, the potassium hydroxide acted as a water soluble pH buffer that adjusted the pH of the final mixed composition to within an acceptable range. The gelling properties of CARBOPOL 974 remained stable for 1–2 weeks within the mixed composition.

Example 5

A two-part dental bleaching system was made that included the following components within each of Parts 1 and 2.

| Part 1 | Part 2 | |
|---|---|---|
| Aqueous hydrogen peroxide (50%) | Glycerin | 79.2 g |
| | CARBOPOL 974 | 4.2 g |
| | Potassium hydroxide | 2.1 g |
| | Carotene | 3.0 g |

Part 1 had a pH below about 2 and was stable against degradation over time. The inclusion of CARBOPOL 974 within Part 2 resulted in a stable viscous gel that did not degrade over time in the presence of potassium hydroxide.

Upon mixing Parts 1 and 2 together in a ratio of 70.5% by weight of Part 1 to 29.5% by weight of Part 2, the potassium hydroxide acted as a water soluble pH buffer that adjusted the pH of the final mixed composition to within an acceptable range. The gelling properties of CARBOPOL 974 remained stable for 1–2 weeks within the mixed composition.

Example 6

A two-part dental bleaching system was made that included the following components within each of Parts 1 and 2.

| Part 1 | Part 2 | |
|---|---|---|
| Aqueous hydrogen peroxide (50%) | Glycerin | 80.4 g |
| | CARBOPOL 974 | 3.0 g |
| | Potassium hydroxide | 2.1 g |
| | Carotene | 3.0 g |

Part 1 had a pH below about 2 and was stable against degradation over time. The inclusion of CARBOPOL 974 within Part 2 resulted in a stable viscous gel that did not degrade over time in the presence of potassium hydroxide, but which was slightly less viscous than Part 2 of Example 5.

Upon mixing Parts 1 and 2 together in a ratio of 70.5% by weight of Part 1 to 29.5% by weight of Part 2, the potassium hydroxide acted as a water soluble pH buffer that adjusted the pH of the final mixed composition to within an acceptable range. The gelling properties of CARBOPOL 974 remained stable for 1–2 weeks within the mixed composition.

Example 7

A two-part dental bleaching system was made that included the following components within each of Parts 1 and 2.

| Part 1 | Part 2 | |
|---|---|---|
| Aqueous hydrogen peroxide (50%) | Glycerin | 81.3 g |
| | CARBOPOL 974 | 2.1 g |
| | Potassium hydroxide | 2.1 g |
| | Carotene | 3.0 g |

Part 1 had a pH below about 2 and was stable against degradation over time. The inclusion of CARBOPOL 974 within Part 2 resulted in a stable viscous gel that did not degrade over time in the presence of potassium hydroxide, but which was slightly less viscous than Part 2 of Example 6.

Upon mixing Parts 1 and 2 together in a ratio of 70.5% by weight of Part 1 to 29.5% by weight of Part 2, the potassium hydroxide acted as a water soluble pH buffer that adjusted the pH of the final mixed composition to within an acceptable range. The gelling properties of CARBOPOL 974 remained stable for 1–2 weeks within the mixed composition.

Example 8

A two-part dental bleaching system was made that included the following components within each of Parts 1 and 2.

| Part 1 | | Part 2 | |
|---|---|---|---|
| Aqueous hydrogen peroxide (50%) | 352.5 g | Glycerin | 95.5 g |
| CARBOPOL 974 | 2.0 g | CARBOPOL 974 | 5 g |
| Glycerin | 35 g | Potassium hydroxide | 5 g |
| | | Carotene | 5 g |

Although the hydrogen peroxide within Part 1 was stable against degradation over time, the CARBOPOL 974 did not result in a stable gel. It is believed that the concentrated hydrogen peroxide attacked or otherwise destroyed the gelling properties of the CARBOPOL 974.

The inclusion of CARBOPOL 974 within Part 2 resulted in a stable viscous gel that did not degrade over time in the presence of potassium hydroxide.

Upon mixing Parts 1 and 2 together in a ratio of 77.9% by weight of Part 1 to 22.1% by weight of Part 2, the potassium hydroxide acted as a water soluble pH buffer that adjusted the pH of the final mixed composition to within an acceptable range. The gelling properties of the portion of CARBOPOL 974 provided by Part 2 remained stable for 1–2 weeks within the mixed composition.

Example 9

A two-part dental bleaching system was made that included the following components within each of Parts 1 and 2.

| Part 1 | | Part 2 | |
|---|---|---|---|
| Aqueous hydrogen peroxide (50%) | 352.5 g | Glycerin | 95.5 g |
| CARBOPOL 974 | 3.5 g | CARBOPOL 974 | 3.5 g |
| Glycerin | 35 g | Potassium hydroxide | 5 g |
| | | Carotene | 5 g |

Although the hydrogen peroxide within Part 1 was stable against degradation over time, the CARBOPOL 974 did not result in a stable gel within Part 1. It is believed that the concentrated hydrogen peroxide attacked or otherwise destroyed the gelling properties of the CARBOPOL 974 within Part 1.

On the other hand, the inclusion of CARBOPOL 974 within Part 2 resulted in a stable viscous gel that did not degrade over time in the presence of potassium hydroxide.

Upon mixing Parts 1 and 2 together in a ratio of 78.2% by weight of Part 1 to 21.8% by weight of Part 2, the potassium hydroxide acted as a water soluble pH buffer that adjusted the pH of the fmal mixed composition to within an acceptable range. The gelling properties of the portion of CARBOPOL 974 provided by Part 2 remained stable for 1–2 weeks within the mixed composition.

Example 10

A two-part dental bleaching system was made that included the following components within each of Parts 1 and 2.

| Part 1 | | Part 2 | |
|---|---|---|---|
| Aqueous hydrogen peroxide (50%) | 352.5 g | Glycerin | 109 g |
| Fumed silica | 25 g | CARBOPOL 974 | 3.5 g |
| PEG 600 | 10 g | Potassium hydroxide | 5 g |
| | | Carotene | 5 g |

Both of Parts 1 and 2 were stable gels. The fumed silica formed a stable gel within Part 1 in the presence of the hydrogen peroxide and PEG 600. The inclusion of CARBOPOL 974 within Part 2 resulted in a stable viscous gel that did not degrade over time in the presence of potassium hydroxide.

Upon mixing Parts 1 and 2 together in a ratio of 75.8% by weight of Part 1 to 24.2% by weight of Part 2, the potassium hydroxide acted as a water soluble pH buffer that adjusted the pH of the final mixed composition to within an acceptable range. The gelling properties of the portion of CARBOPOL 974 provided by Part 2 remained stable for 1–2 weeks within the mixed composition. The viscosity of the mixed composition was considerably higher than the viscosities of Examples 1–9.

Example 11

A two-part dental bleaching system was made that included the following components within each of Parts 1 and 2.

| Part 1 | | Part 2 | |
|---|---|---|---|
| Aqueous hydrogen peroxide (50%) | 352.5 g | Glycerin | 118.5 g |
| Fumed silica | 17.5 g | CARBOPOL 974 | 1.5 g |
| | | Potassium hydroxide | 5 g |
| | | Carotene | 5 g |

Both of Parts 1 and 2 were stable gels. The fumed silica formed a stable gel within Part 1 in the presence of the aqueous hydrogen peroxide. The inclusion of CARBOPOL 974 within Part 2 resulted in a stable viscous gel that did not degrade over time in the presence of potassium hydroxide.

Upon mixing Parts 1 and 2 together in a ratio of 75.8% by weight of Part 1 to 24.2% by weight of Part 2, the potassium hydroxide acted as a water soluble pH buffer that adjusted the pH of the final mixed composition to within an acceptable range. The gelling properties of the portion of CARBOPOL 974 provided by Part 2 remained stable for 1–2 weeks within the mixed composition. The fumed silica and CARBOPOL 974 within the mixed composition worked well together to yield a mixed composition having good viscosity and stickiness.

Example 12

A two-part dental bleaching system was made that included the following components within each of Parts 1 and 2.

| Part 1 | | Part 2 | |
|---|---|---|---|
| Aqueous hydrogen peroxide (50%) | 352.5 g | Glycerin | 114 g |
| | | CARBOPOL 974 | 2.25 g |
| Fumed silica | 17.5 g | Potassium hydroxide | 5 g |
| | | Carotene | 5 g |

Both of Parts 1 and 2 were stable gels. The fumed silica formed a stable gel within Part 1 in the presence of the aqueous hydrogen peroxide. The inclusion of CARBOPOL 974 within Part 2 resulted in a stable viscous gel that did not degrade over time in the presence of potassium hydroxide.

Upon mixing Parts 1 and 2 together in a ratio of 75.8% by weight of Part 1 to 24.2% by weight of Part 2, the potassium hydroxide acted as a water soluble pH buffer that adjusted the pH of the final mixed composition to within an acceptable range. The gelling properties of the portion of CARBOPOL 974 provided by Part 2 remained stable for 1–2 weeks within the mixed composition. The fumed silica and CARBOPOL 974 within the mixed composition worked well together to yield a mixed composition having good viscosity and stickiness.

Example 13

A two-part dental bleaching system was made that included the following components within each of Parts 1 and 2, measured in terms of weight % of the final mixed composition.

| Part 1 | | Part 2 | |
|---|---|---|---|
| Aqueous hydrogen peroxide (50%) | 70.5% | Glycerin | 21.4% |
| Fumed silica | 5.0% | CARBOPOL 974 | 0.3% |
| PEG 600 | 0.3% | Potassium hydroxide | 1.5% |
| | | Carotene | 1.0% |

Both of Parts 1 and 2 were stable gels. The fumed silica and PEG 600 resulted in Part 1 being a stable gel in the presence of the aqueous hydrogen peroxide. The inclusion of CARBOPOL 974 within Part 2 resulted in a stable viscous gel that did not degrade over time in the presence of potassium hydroxide.

Upon mixing Parts 1 and 2 together to yield a final mixed composition that included the foregoing components added in the amounts given above, the potassium hydroxide acted as a water soluble pH buffer that adjusted the pH of the final mixed composition to 7.03. The gelling properties of the portion of CARBOPOL 974 provided by Part 2 remained stable for 1–2 weeks within the mixed composition. The fumed silica, CARBOPOL 974 and PEG 600 within the mixed composition worked well together to yield a mixed composition having good viscosity and stickiness. The mixed composition was relatively stable over time, particularly when refrigerated.

Example 14

A two-part dental bleaching system was made that included the following components within each of Parts 1 and 2, measured in terms of weight % of the final mixed composition.

| Part 1 | | Part 2 | |
|---|---|---|---|
| Aqueous hydrogen peroxide (50%) | 70.5% | Glycerin | 19.9% |
| Fumed silica | 5.0% | CARBOPOL 974 | 0.3% |
| PEG 600 | 0.3% | Potassium hydroxide | 2.0% |
| Citric Acid | 1.0% | | |
| | | Carotene | 1.0% |

Both of Parts 1 and 2 were stable gels. The fumed silica, PEG 600 and citric acid resulted in Part 1 being a stable gel in the presence of the aqueous hydrogen peroxide. The inclusion of CARBOPOL 974 within Part 2 resulted in a stable viscous gel that did not degrade over time in the presence of potassium hydroxide.

Upon mixing Parts 1 and 2 together to yield a final mixed composition that included the foregoing components added in the amounts given above, the potassium hydroxide acted as a water soluble pH buffer that adjusted the pH of the final mixed composition to 7.75. The gelling properties of the portion of CARBOPOL 974 provided by Part 2 remained stable for 1–2 weeks within the mixed composition. The fumed silica, CARBOPOL 974 and PEG 600 within the mixed composition worked well together to yield a mixed composition having good viscosity and stickiness. The mixed composition was relatively stable over time, particularly when refrigerated, which was due, in part, to the inclusion of the citric acid.

Example 15

A two-part dental bleaching system was made that included the following components within each of Parts 1 and 2, measured in terms of weight % of the final mixed composition.

| Part 1 | | Part 2 | |
|---|---|---|---|
| Aqueous hydrogen peroxide (50%) | 70.5% | Glycerin | 20.38% |
| Fumed silica | 5.0% | CARBOPOL 974 | 0.32% |
| PEG 600 | 0.3% | Potassium hydroxide | 3.0% |
| | | Carotene | 0.5% |

Both of Parts 1 and 2 were stable gels. The fumed silica and PEG 600 resulted in Part 1 being a stable gel in the presence of the aqueous hydrogen peroxide. The inclusion of CARBOPOL 974 within Part 2 resulted in a stable viscous gel that did not degrade over time in the presence of potassium hydroxide.

Upon mixing Parts 1 and 2 together to yield a final mixed composition that included the foregoing components added in the amounts given above, the potassium hydroxide acted as a water soluble pH buffer that adjusted the pH of the final mixed composition to 8.20. The gelling properties of the portion of CARBOPOL 974 provided by Part 2 remained stable for 1–2 weeks within the mixed composition. The fumed silica, CARBOPOL 974 and PEG 600 within the mixed composition worked well together to yield a mixed composition having good viscosity and stickiness. The mixed composition was relatively stable over time, particularly when refrigerated.

Example 16

Any of the foregoing two-part bleaching systems described in Examples 1–15 is modified by eliminating the polyol (e.g., glycerin or propylene glycol) in order for the neutralizing composition of Part 2 to comprise a dry mixture of solid components.

Upon mixing Parts 1 and 2 together, the base (KOH) neutralizes the acidic hydrogen peroxide composition to a desired pH and the tackifying agent (e.g., PEMULEN or CARBOPOL 974) imparts a desired tackifying, thickening and gel properties to the final mixed composition.

Example 17

Any of the foregoing two-part bleaching systems described in Examples 1–16 is modified by substituting potassium hydroxide within Part 2 with an appropriate quantity of calcium carbonate in particulate form.

Example 18

Any of the foregoing two-part bleaching systems described in Examples 16 and 17 is modified by adding or replacing a portion of the polymeric thickening agent of Part 2 with fumed silica or fumed aluminum oxide.

V. SUMMARY

The present invention provides improved multi-part dental bleaching systems and methods of manufacturing such systems in order to yield a mixed composition having a high peroxide content desired gel properties as a result of including a polymeric thickening agent.

The invention further provides multi-part systems that can be manufactured so as to yield at least one component that includes a strong base and a polymeric thickening agent without premature degradation of the thickening agent.

The invention also provides a concentrated low pH aqueous hydrogen peroxide bleaching composition in one part and a strong base in another part for mixing with and at least partially neutralizing the acidic bleaching composition prior to use.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A multi-part dental bleaching system comprising:
   an aqueous dental bleaching composition that includes at least one dental bleaching agent and that has an acidic pH; and
   a substantially water free neutralizing composition suitable for mixing with the aqueous dental bleaching composition and that comprises at least one polymeric thickening agent mixed with at least one particulate base selected from the group consisting of metal oxides, metal hydroxides, ammonium hydroxide, and metal carbonates.

2. A multi-part dental bleaching system as defined in claim 1, the dental bleaching composition comprising at least about 20%, by weight of the system, of available hydrogen peroxide.

3. A multi-part dental bleaching system as defined in claim 1, the dental bleaching composition comprising at least about 30%, by weight of the system, of available hydrogen peroxide.

4. A multi-part dental bleaching system as defined in claim 1, the dental bleaching composition comprising at least about 40%, by weight of the system, of available hydrogen peroxide.

5. A multi-part dental bleaching system as defined in claim 1, the dental bleaching composition having a pH of about 4 or less.

6. A multi-part dental bleaching system as defined in claim 1, the dental bleaching composition having a pH of about 3 or less.

7. A multi-part dental bleaching system as defined in claim 1, the dental bleaching having a pH of about 1–2.

8. A multi-part dental bleaching system as defined in claim 1, at least one of the dental bleaching composition or the neutralizing composition further comprising at least one ion scavenger.

9. A multi-part dental bleaching system as defined in claim 8, the ion scavenger comprising at least one of EDTA or citric acid.

10. A multi-part dental bleaching system as defined in claim 1, the particulate base comprising at least one of an alkali metal oxide, an alkali metal hydroxide, an alkaline earth metal oxide, or an alkaline earth metal hydroxide.

11. A multi-part dental bleaching system as defined in claim 1, the polymeric thickening agent comprising at least one of an acrylic acid polymer or carboxypolymethylene.

12. A multi-part dental bleaching system as defined in claim 11, the at least one acrylic acid polymer comprising a cross-linked acrylic acid copolymer.

13. A multi-part dental bleaching system as defined in claim 1, the polymeric thickening agent comprising at least one of a pluronic, a cellulosic ether, a polysaccharide gum, a protein or starch.

14. A multi-part dental bleaching system as defined in claim 1, wherein the neutralizing composition further comprising a radiant energy absorbing agent.

15. A multi-part dental bleaching system as defined in claim 14, the radiant energy absorbing agent comprising at least one dye.

16. A multi-part dental bleaching system as defined in claim 1, at least one of the dental bleaching composition or neutralizing composition further comprising a polyol.

17. A multi-part dental bleaching system as defined in claim 16, the polyol comprising at least one of glycerin, sorbitol, propylene glycol, polyethylene glycol, or polypropylene glycol.

18. A multi-part dental bleaching system as defined in claim 1, at least one of the dental bleaching composition or neutralizing composition further comprising flumed silica.

19. A multi-part dental bleaching system as defined in claim 1, the dental bleaching system being in the form of a kit that comprises the dental bleaching composition in a first part and the neutralizing composition in a second part.

20. A multi-part dental bleaching system as defined in claim 19, the kit comprising at least one syringe containing the dental bleaching composition and at least one additional syringe containing the neutralizing composition.

21. A multi-part dental bleaching system as defined in claim 19, the kit comprising at least one dual compartment syringe containing the dental bleaching composition in a first compartment and the neutralizing composition in a second compartment.

22. A multi-part dental bleaching system as defined in claim 19, at least one of the dental bleaching composition or neutralizing composition being free of abrasives.

23. A multi-part dental bleaching system as defined in claim 1, the neutralizing composition being a non-gelled mixture of dry solid components.

24. A multi-part dental bleaching system comprising:
an aqueous dental bleaching composition that comprises at least one dental bleaching agent and that has a pH of less than 4; and
a substantially water free neutralizing composition suitable for mixing with the dental bleaching composition and that comprises at least one particulate base mixed with at least one thickening agent to form a mixture of dry solids.

25. A multi-part dental bleaching system comprising:
an aqeous dental bleaching composition that includes at least about 30%, by weight of the system, of available hydrogen peroxide and that has an acidic pH; and
a substantially water free neutralizing composition suitable for mixing with the dental bleaching composition comprising at least one particulate base mixed with at least one polymeric thickening agent to form a non-gelled mixture of dry solids.

26. A multi-part dental bleaching system as defined in claim 25, wherein the dental bleaching composition has a pH of less than about 3.

27. A multi-part dental bleaching system as defined in claim 25, wherein the thickening agent comprises at least one of an acrylic acid polymer or carboxypolymethylene.

28. A method of manufacturing a multi-part dental bleaching system comprising:
(a) preparing a dental bleaching composition that comprises a dental bleaching agent and that has an acidic pH; and
(b) preparing a neutralizing composition suitable for mixing with the dental bleaching composition by combining at least one alkaline base with at least one polymeric thickening agent yield a dry mixture of solids that is substantially water free and c) including said dental bleaching composition and said neutralizing composition in a multi-part dental bleaching system.

29. A method of manufacturing a multi-part dental bleaching system as defined in claim 28, the alkaline base comprising at least one of an alkali metal oxide, an alkali metal hydroxide, an alkaline earth metal oxide, ammonium hydroxide, or an alkaline earth metal hydroxide.

30. A method of manufacturing a multi-part dental bleaching system as defined in claim 28, the polymeric thickening agent comprising at least one of an acrylic acid polymer or carboxypolymethylene.

31. A method of bleaching a person's teeth comprising:
(1) providing a multi-part dental bleaching system comprising:
a dental bleaching composition that comprises a dental bleaching agent and that has a pH of less than 4; and
a substantially water free neutralizing composition suitable for mixing with the dental bleaching composition and that comprises at least one particulate based mixed with at least one polymeric thickening agent;
(2) mixing together the dental bleaching composition and the neutralizing composition to yield a mixed composition having a pH in a range of about 4 to about 11 and that comprises a sticky gel; and
(3) applying the mixed composition comprising the sticky gel to at least a portion of the person's teeth.

* * * * *

UNITED STATES PATENT AND TRADEMARK OFFICE
CERTIFICATE OF CORRECTION

PATENT NO. : 6,746,664 B2
DATED : June 8, 2004
INVENTOR(S) : Peter M. Allred

It is certified that error appears in the above-identified patent and that said Letters Patent is hereby corrected as shown below:

Column 1,
Line 30, after "except at" insert -- a --
Line 46, after "and/or kept at" insert -- a --

Column 5,
Line 60, after "and at" insert -- a --

Column 13,
Line 64, after "pH of the" change "fmal" to -- final --

Column 18,
Line 55, after "comprising" change "flumed" to -- fumed --

Signed and Sealed this

Seventh Day of December, 2004

JON W. DUDAS
*Director of the United States Patent and Trademark Office*